United States Patent
Eibl

[11] Patent Number: 5,916,884
[45] Date of Patent: Jun. 29, 1999

[54] COMPOSITIONS CONTAINING A MIXTURE OF PHOSPHORUS COMPOUNDS AND ALKYLGLYCEROLS

[75] Inventor: Hansjörg Eibl, Bovenden, Germany

[73] Assignee: Max-Planck-Gesellschaft Zur Foederung Der Wissenschaften, Gottingen, Germany

[21] Appl. No.: 08/458,232

[22] Filed: Jun. 2, 1995

Related U.S. Application Data

[62] Division of application No. 08/257,687, Jun. 9, 1994, abandoned, which is a continuation-in-part of application No. 07/912,554, Jul. 13, 1992, abandoned, which is a continuation-in-part of application No. 07/517,440, May 1, 1990, abandoned, which is a continuation of application No. 07/096,918, Oct. 2, 1987, abandoned, filed as application No. PCT/EP86/00706, Dec. 4, 1986.

[30] Foreign Application Priority Data

Feb. 28, 1986 [DE] Germany ............... 36 06 631
Dec. 4, 1995 [DE] Germany ............... 35 42 893

[51] Int. Cl.$^6$ ................................. A61K 31/685
[52] U.S. Cl. ............................................... 514/77
[58] Field of Search ................................. 514/77

[56] References Cited

U.S. PATENT DOCUMENTS 4,837,023 6/1989 Eibl ........................... 514/77 X
4,935,520 6/1990 Nojima et al. ................. 546/22

OTHER PUBLICATIONS

C. Unger et al. Klinische Wochenschrift, 63, 565–571 (1985).
K. Ando et al. Cancer Research. 32, 125–129 (1972).

*Primary Examiner*—Michael G. Ambrose
*Attorney, Agent, or Firm*—Fulbright & Jaworski, LLP

[57] ABSTRACT

Cytotoxic therapeutic compositions contain as active ingredients compounds of the formula $$R—Y—PO^\ominus_2—X—R_1$$

wherein R is a saturated or unsaturated hydrocarbon radical of 12 to 14 carbon atoms which may also be halogen-substituted, X is oxygen, —NH— or —NR$_2$—, Y is oxygen or —NH— and R$_1$ has diverse meanings or physiologically acceptable salts thereof.

4 Claims, No Drawings

COMPOSITIONS CONTAINING A MIXTURE OF PHOSPHORUS COMPOUNDS AND ALKYLGLYCEROLS

CROSS REFERENCE TO RELATED APPLICATIONS

This application is a division of application Ser. No. 08/257,687, filed Jun. 9, 1994, now abandoned, which is a continuation-in-part of application Serial No. 07/912,554, filed Jul. 13, 1992, now abandoned; which in turn is a continuation-in-part of Ser. No. 07/517,440, filed May 1, 1990, now abandoned; which in turn is a continuation of application Ser. No. 07/096,918, filed Oct. 2, 1987, now abandoned which was filed as PCT/EP86/00706 on Dec. 4, 1986.

FIELD OF THE INVENTION

This invention relates to novel therapeutic compositions having activity as a biological response modifier, which are especially suitable for the treatment of tumors.

BACKGROUND OF THE INVENTION

European Application 108 565 concerns compounds of the formula

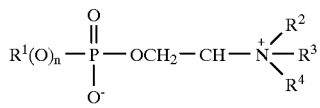

wherein $R^1$ is an aliphatic $C_8$–$C_{30}$-hydrocarbon radical and $R^2$, $R^3$ and $R^4$ are hydrogen, lower alkyl, the group

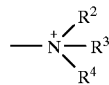

or a cyclic ammonium radical, and n=0. For these compounds, it is stated that they inhibit the proliferation of tumor cells and prolong the life span of warm-blooded animals which have such tumors; furthermore an anti-fungal action is mentioned.

It is known that heretofore no medicament for the treatment of tumors, especially of malignant tumors, was available which was satisfactory in all respects. Thus for example, for the topical treatment of skin metastases in patients with metastasizing tumors, at present only 5-fluorouracil is available. Further developments of other cytostatics have heretofore not progressed to clinical maturity for this manner of administration. On the other hand, from a clinical point of view, such a concept of palliative therapeutic use is especially desirable since alternative concepts of treatment, such as surgical measures, radiation therapy and systemic chemotherapy, constitute comparatively aggressive therapy modalities Furthermore, a considerable number of patients are available as potential treatment candidates for such a topical treatment Thus, the proportion of mammary carcinoma patients who display a skin attack amounts to about 25 to 35%.

The prerequisites for topical treatment on the part of the active material to be used are compatibility with the skin, cytotoxic effectiveness against tumor cells and sufficiently deep penetration.

OBJECTS OF THE INVENTION

The object of the invention is to provide a medicament which is suitable for the topical treatment of tumors.

Another object of the invention is to provide a medicament which, in general, can also be used in other forms of administration which combines a good effectiveness against tumors with lower toxicity and can, therefore, be generally used in tumor therapy.

Other objects and advantages of the invention will become apparent as the description thereof proceeds.

DESCRIPTION OF THE INVENTION

These objects are, according to the invention, achieved by a medicament which contains as active material at least one compound of the formula

as defined below except hexadecylphosphocholine, or a physiologically acceptable salt hereof, optionally together with conventional pharmacological additives and diluents. Preferred active materials, are oleylphosphocholine or hexadecylphosphoric acid-(N,N)-bis-(2-chloroethyl)-amide.

The formula also includes the possible enantiomers and diastereoisomers. If the compounds are racemates, these can be resolved in the usual way, for example by means of an optically active acid, into the optically active isomers. Preferably, however, enantiomeric or optionally diastereoisomeric starting materials are used, whereby the end product is obtained as a corresponding pure optically active or diastereoisomeric compound.

In the scope of the invention, R is preferably an alkyl group of the given chain length which is linked with the oxygen atom of the glycol residue via a terminal C-atom or also via a C-atom within the alkyl chain (for example via the C-atom 2 or C-atom 3 or another middle C-atom). This alkyl chain can be straight or branched. The alkyl chain R can contain one, two or three carbon double bonds or triple bonds, which can also be present mixed, and/or halogen substituents such as fluorine, chlorine or bromine One to three of such halogen atoms can be present in the chain R, and these can be present on one or on different C-atoms of the radical R.

Besides the saturated straight alkyl radicals, those are preferred with one or two carbon double bonds in the molecules Especially preferred are those substituents R which contain an alkyl radical with 14 to 20, preferably 15 to 20, especially 16 to 20 C-atoms or a corresponding alkenyl radical with 14 to 20, preferably 15 to 20, especially 16 to 20 C-atoms.

Examples of halogen-substituted radicals R are: chlorohexadecyl, bromohexadecyl, fluorohexadecyl, 9,1-dibromooctadecyl, 2,3-dibromooctadecyl, 15,16-dibromohexadecyl, and bromotetradecyl.

Examples of unsaturated radicals R are: 9-octadecenyl radical (oleyl alcohol radical, in formula I or I', R especially signifies this 9-octadecenyl radical), 15-decadecenyl radical, 9,12-octadecadienyl radical (linoleyl radical).

If more than one double or triple bond is present, these are conjugated.

Examples of saturated and unsubstituted radicals R are tetradecyl, hexadecyl and octadecyl.

If $R_1$ or $R_2$ signify an unsubstituted alkyl group, this consists, for example, of 1–6, preferably 1–4 C-atoms. If $R_1$ or $R_2$ signify an unsaturated alkyl group, it consists especially of 3 to 6 C-atoms, where, between the unsaturated function of such an unsaturated alkyl group and X, there must be present at least one single C—C bond. In particular, they are $C_3$–$C_6$-alkylene groups. Examples therefor are: allyl, butenyl, pentenyl and hexenyl.

If $R_1$ or $R_2$ are substituted, they are especially straight-chained alkyl or alkenyl radicals, $R_1$ in this case preferably consisting of 2–6 C-atoms, where the given substituents preferably stand in the ω-position of the alkyl or alkenyl group $R_1$ or $R_2$, for example, it is the ethyl or straight propyl radical with one of the given substituents in ω-position (that is, in 2-position in the case of ethyl and 3-position in the case of propyl) If $R_1$ is a 2-tert.-butyloxycarbonylaminoethyl radical or a 2-tert.-butyloxycarbonylethyl radical, it is preferably the D- or L-form.

Amongst the substituents of $R_1$, the trialkylammonium-ethyl radicals are preferred when X is an oxygen atom, where the trialkyl radicals preferably each consist of one, two or three C-atoms, preferably methyl groups. In this especially preferred embodimental form they are, in the case of formula I, phosphatidylcholine derivatives.

In the case of the $C_3$–$C_8$-cycloalkyl substituents, this consists especially of 3–6 C-atoms (for example, cyclopropyl to cyclohexyl). In the case of the 2,3-dihydroxypropyl-(1) group, it is especially the sn-12-dihydroxypropylamino-(3) structure or the sn-2,3-dihydroxypropylamino-(1) structure.

The active materials of the formula I' are new compounds. Of these new compounds, the following are preferred: oleyl-phospho-(N,N,N-trimethyl)-propanolamine, oleylphospho(N,N,N-trimethyl)-butanolamine, oleylphospho(N,N,N-trimethyl)-pentanolamine, oleylphosphoserine, oleylphosphoethanolamine, oleylphosphopropanolamine, oleylphosphobutanolamine, oleylphosphoglycerol, hexadecylphospho-(N N,N-trimethyl)-propanolamine.

The salts may be internal salts (for example, when $R_1$ is a trimethylammoniumalkyl group) or salts with physiologically acceptable cations. The compounds of this invention can be present as internal salts, for example when $R_1$ contains an amino group. If no internal salts are present or $R_1$ does not contain a basic groups the negative charge of the phosphoric acid group is satisfied by a physiologically acceptable cation. Suitable physiologically acceptable cations are, for example, alkali metal cations (Na, K), alkaline earth metal cations (Mg, Ca) or the cations of organic amines, such as guanidinium, morpholinium, cyclohexylammonium cation, ethylenediammonium cation, piperazonium cation (in the two latter cases, mono- or dibasic) or the cation which is derived from an amine of the formula $NR_aR_bR_c$, wherein $R_a$, $R_b$ and $R_c$ are the same or different and represent hydrogen, $C_1$–$C_2$-alkyl groups or oxyethyl groups. If it is a cation which is derived from an amine of the formula $NR_aR_bR_c$, it is preferably the ammonium cation or an ammonium cation substituted with one to three $C_1$–$C_2$-alkyl groups or an ammonium cation substituted with one to three 2-hydroxyethyl groups.

The preparation of the compounds of the formulas I and I' can take place by known methods. The basic structure can easily be obtained by reaction of a compound of the formula RO or a functional derivative hereof with phosphorus oxychloride and triethylamine, reaction of the product with a compound $HXR_1$ and acid cleavage, where R, $R_1$ and X have the meanings previously defined below.

The preparation process for the compounds of formulas I and I' is schematically illustrated, for example, in the following reaction equations: (the group $OCH_3$ in the various formulas stands representatively for the group OZ).

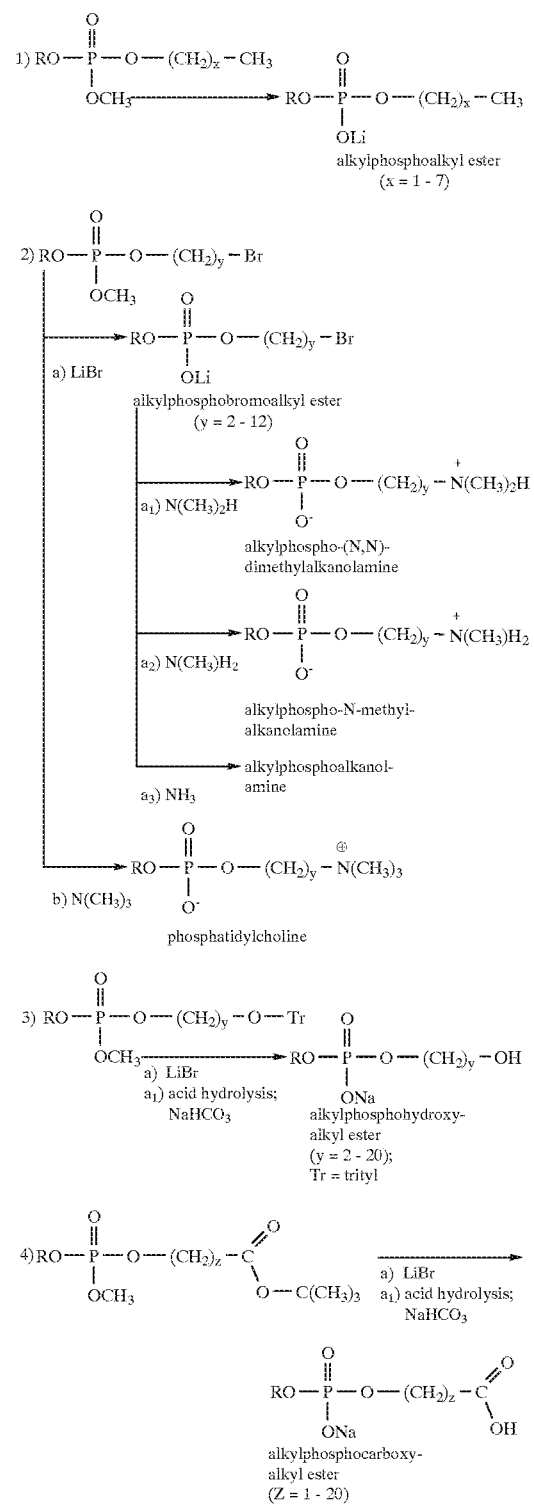

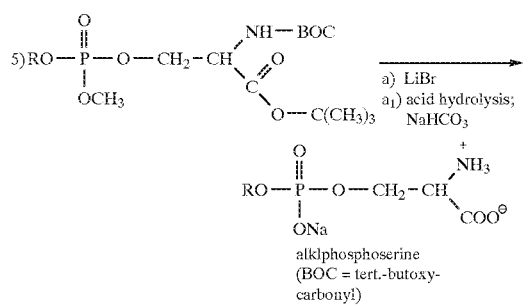
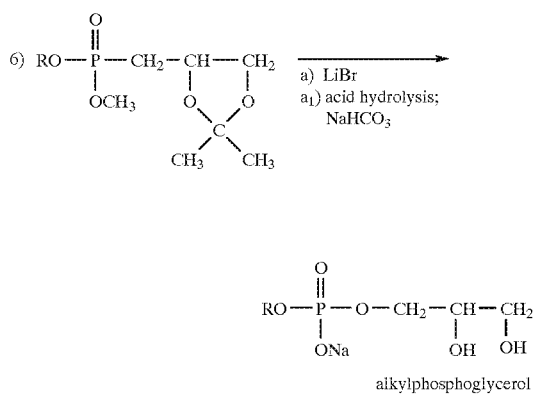
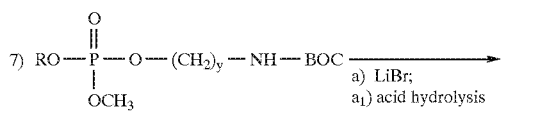
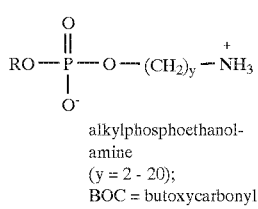
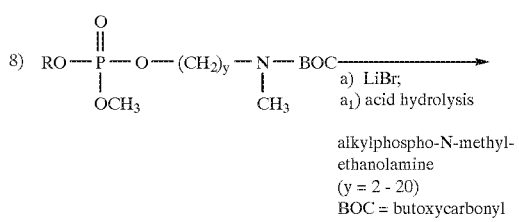
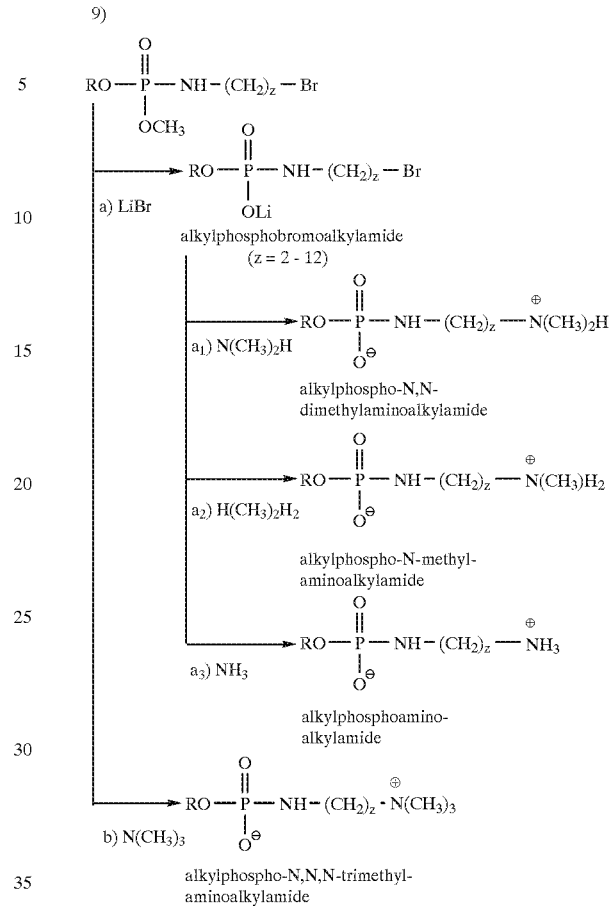

In the starting compounds of the formula III, as defined in claim 9, hydroxyl groups, carboxyl groups, amino groups or $C_1$–$C_6$-alkylamino groups, which occur in the radical $R^1$ or also in the radical $R^2$ (if X is the group $NR^2$), can be protected by conventional protective groups. Neighboring hydroxyl groups can be protected by ketalization with an aliphatic saturated $C_3$–$C_6$-ketone.

The protective groups are radicals which can easily be split off by hydrolysis or hydrogenation and are split off during or after the reaction. If such protective groups are not split off during the process reaction, then a splitting off takes place after the reaction. The starting compounds frequently contain such protective groups by virtue of their preparation.

These protective groups are, for example, acyl groups which can easily be split off solvolytically or groups which can be split off by hydrogenation. The protective groups which can be split off solvolytically are, for example, split off by hydrolysis with dilute acids (for example, acetic acid, perchloric acid, hydrochloric acid, sulfuric acid, formic acid, trifluoroacetic acid) or by means of basic substances (potash, soda, aqueous alkali solutions, alcoholic alkali solutions, $NH_3$) at temperatures between –50 and 150° C., especially between 0 and 100° C. Groups which can be split off by hydrogenation, such as arylalkyl radicals (benzyl) or hydroxycarbonyl radicals (carbobenzoxy), are expediently split off by catalytic hydrogenation in the presence of conventional hydrogenation catalysts (noble metal catalysts) especially palladium catalysts or also platinum catalysts (platinum oxide), or Raney nickel, in a solvent or suspension agent,, possibly under elevated pressure (for example 1–50 bar) at temperatures between 20–150° C., especially 30–100° C., preferably 40–80° C.

Suitable solvents or suspension agents for splitting off such protective groups are, for example, water, lower aliphatic alcohols, cyclic ethers, such as dioxane or tetrahydrofuran, aliphatic ethers, halogenated hydrocarbons, dimethylformamide and so forth, as well as mixtures of these agents. Suitable protective groups which can be split off by hydrogenation are, for example, benzyl, α-phenylethyl, benzyl substituted in the benzene nucleus (p-bromo- or p-nitrobenzyl radical), carbobenzoxy, carbobenzthio and tert.butyloxycarbonyl. Examples of radicals which can be split off by hydrolysis are trifluoroacetyl, phthalyl, trityl, p-toluenesulfonyl, tert.butyloxycarbonyl, tert.butyl, dimethylmethylene and the like, as well as lower alkanoyl, such as acetyl, formyl, tert.butylcarboxy and the like.

In particular, the protective groups conventionally used in peptide syntheses and methods for their removal may be employed. In this regard, reference is made to Jesse P. Greenstein and Milton Winitz "Chemistry of Amino Acids", New York 1961, John Wiley and Sons, Inc., Volume 2, for example page 883 et seq. The carbalkoxy group (for example low molecular) is also suitable.

The splitting off of the group OZ (this is preferably OCH$_3$) takes place, for example, with alkali metal bromides or iodides, lower alkyl magnesium halides or with primary, secondary or tertiary amines, especially the corresponding lower alkylamines, such as tertiary $C_1$–$C_6$-alkylamines (trimethylamine). Suitable alkali metal bromides or alkali metal iodides are, for example, lithium bromide, sodium bromide, lithium iodide or sodium iodide. Suitable lower alkyl magnesium halides are, for example, methyl magnesium iodide, methyl magnesium bromide (solvents for these are lower aliphatic ethers, such as diethyl ether).

The splitting off of the group OZ from a compound of the formula III takes place at temperatures between 10 and 150° C. preferably 10 and 80° C., especially 50 and 80° C.; the reaction product obtained thereby is, after removal of the solvent, the dissolved in an inert agents Suitable such inert agents are saturated aliphatic $C_3$–$C_8$-ketones (ethyl methyl ketone, diethyl ketone, acetone), cyclic ethers, non-cyclic lower aliphatic ethers (for example diethyl ether) Per 1 mol of compound III, 1.5 to 3 mols of the previously mentioned cleavage agents, preferably 2 mols, are generally used.

The reaction of products obtained (for example compounds in which $R^1$ and/or $R^2$ are haloalkyl) with ammonia or with an amine of the formula $NR^3R^4R^5$ takes place at temperatures between 10 and 200, preferably 20 and 150° C., especially 40 and 80° C., with or without solvents. If a solvent or suspension agent is used, suitable examples are aromatic hydrocarbons, such as pentane, hexane, heptane benzene, mesitylene, toluene or xylene; lower aliphatic ketones, such as acetone or methyl ethyl ketone; halogenated hydrocarbons, such as chloroform, trichloroethylene, carbon tetrachloride, chlorobenzene or methylene chloride; cyclic ethers, such as tetrahydrofuran or dioxane; lower aliphatic non-cyclic ethers (diethyl ether, diisopropyl ether); lower aliphatic alcohols (1–6 C-atoms), such as methanol, ethanol, isopropanol, amyl alcohol, butanol, tert.butanol; amides and N-alkyl-substituted amides of aliphatic $C_1$–$C_4$-carboxylic acids (dimethylformamide, dimethylacetamide); $C_1$–$C_6$-dialkylsulfones (dimethyl sulfone, tetramethyl sulfone); $C_1$–$C_6$-dialkyl sulfoxides (dimethyl sulfoxide), as well as other aprotic agents, such as N-methyl-pyrrolidone, tetramethylurea, hexamethylphosphoric acid triamide or acetonitrile. The individual alkyl radicals of the above-mentioned solvents contain, for example, 1–6, especially 1–4 carbon atoms. Mixtures of these agents, as well as mixtures with water, are also suitable as reaction medium. The reaction is carried out, for example, at temperatures of 0 to 200° C., preferably 20 to 150° C. or also 50 to 120° C. If a solvent or dispersion agent is used, it is performed at the reflux temperature of this agent.

The amination reaction is expediently carried out in the presence of basic materials, such as alkali metal hydroxides, alkali metal carbonates or tertiary amines.

The alkylation of free amino groups in the radicals $R^1$ and/or $R^2$ takes place at temperatures between 0 and 200° C., preferably between 20 and 150° C., especially between 20 and 80° C. This alkylation takes place, for example, by reaction with a compound of the formula R'Hal, ArSO$_2$OR' and SO$_2$(OR'$_3$)$_2$, where Hal is a halogen atom (especially chlorine, bromine or iodine) and Ar is an aromatic radical (for example phenyl or naphthyl, optionally substituted by one or more lower alkyl radicals) and R' is $C_1$–$C_6$-alkyl. Examples are p-toluenesulfonic acid $C_1$–$C_6$-alkyl esters, $C_1$–$C_6$-dialkyl sulfates and $C_1$–$C_6$-alkyl halides. The alkylation reaction is optionally carried out in the presence of conventional acid-binding agents, such as alkali metal hydroxides, alkali metal carbonates, alkali metal bicarbonates, alkaline earth metal carbonates, alkali metal acetates, tertiary amines (for example trialkylamine, such as triethylamine), pyridine or also alkali metal hydrides in inert solvents or suspension agents Suitable solvents or dispersion agents are, for example, aromatic hydrocarbons, such as benzene, toluene or xylene; aliphatic ketones, such as acetone, a methyl ethyl ketone, halogenated hydrocarbons, such as chloroform, carbon tetrachloride, chlorobenzene or methylene chloride; aliphatic ethers, such as butyl ether; cyclic ethers, such as tetrahydrofuran or dioxane; sulfoxides, such as dimethyl sulfoxide; tertiary acid amides, such as dimethyl formamide, N-methylpyrrolidone or hexamethylphosphoric acid triamide; aliphatic alcohols, such as methanol, ethanol, isopropanol, amyl alcohol or tert.butanol; cycloaliphatic hydrocarbons, such as cyclohexane and the like. Aqueous mixtures of the said solvents can also be used. The reaction is advantageously performed at the reflux temperature of the particular solvent or dispersion agent. The alkylation reaction components are advantageously used in excess. The alkylation can also be carried out in the presence of tetraalkylammonium salts (especially of the halides) in combination with alkali metal hydroxides at temperatures between 0–100° C., preferably 20–80° C., in an aprotic solvent or also in chloroform or methylene chloride. Suitable aprotic solvents are especially tertiary amides (dimethylformamide, N-methylpyrrolidone, hexamethylphosphoric acid triamide), dimethyl sulfoxide, acetonitrile, dimethoxyethane, acetone or tetrahydrofuran.

The compounds of the formula I or I' contained in the compositions according to the present invention are, in part, novel and also an object of the invention. They exhibit an outstanding cytotoxic effectiveness which has been demonstrated not only in vivo on chemically-induced mammary carcinoma of the rat, but also in vitro on leukemia cells in the cell culture. Furthermore, in a clinical pilot study on female patients with mammary carcinoma, skin metastases were brought to complete healing by topical application.

The following compounds and their physiologically acceptable salts are novel.

Compounds of the formula $$R-Y-PO^{\ominus}{}_2-X-R_1 \quad (I')$$

wherein R is a saturated or unsaturated hydrocarbon radical of 12 to 24 C-atoms which may be halogen-substituted, X is oxygen, —NH— or —NR$_2$—, Y is oxygen or —NH—, R$_1$ is a) a $C_1$–$C_8$-alkyl group, an unsaturated $C_3$–$C_8$-alkyl group or an optionally unsaturated $C_3$–$C_8$-alkyl group which is substituted by halogen, $C_1$–$C_6$-alkylamino, di-$C_1$–$C_6$-alkylamino, tri-$C_1$–$C_6$-alkylamino, hydroxyl, carboxyl, $C_3$–$C_8$-cycloalkyl or phenyl, or b) a $C_2$-alkyl group which is substituted by halogen, hydroxyl, carboxyl, $C_3$–$C_8$-cycloalkyl or phenyl, or c) an unsaturated $C_2$-alkyl group which is substituted by di-$C_1$–$C_6$-alkylamino, tri-$C_1$–$C_6$-alkylamino, carboxyl, $C_3$–$C_8$-cycloalkyl or phenyl, or d) a $C_2$-alkyl group which is substituted by amino, $C_1$–$C_6$-alkylamino, di-$C_1$–$C_6$-alkylamino or tri-$C_1$–$C_6$-alkylamino if X is oxygen, —NH— or —NR$_2$—, and Y is —NH—, or if X is —NR$_2$—, Y is oxygen, and R has the given meanings, or e) 2-tert.butyloxycarbonylaminoethyl, 2-tert.butyloxycarbonylethyl, 2,3-isopropylidenedioxypropyl-(1), 2,3-dibenzyloxypropyl-(1), 1,3-dibenzyloxypropyl-(2) or N—$C_1$–$C_6$-alkylamino-$C_2$–$C_6$-alkyl if X is oxygen and Y and R have the given meanings, or f) 2,3-dihydroxypropyl-(1) if X is —NH— and Y and R have the given meanings, and R$_2$ is 2,3-dihydroxypropyl-(1), $C_1$–$C_8$-alkyl or $C_2$–$C_8$-alkyl which is unsaturated and/or substituted with halogen, amino, $C_1$–$C_6$-alkylamino, Di-$C_1$–$C_6$-alkylamino, tri-$C_1$–$C_6$-alkylamino, hydroxyl, carboxyl, $C_3$–$C_8$-cycloalkyl or phenyl, provided that those compounds are excluded where, in formula I', X and Y are both oxygen, R$_1$— is a saturated or unsaturated $C_1$–$C_8$-alkyl radical which can also be substituted by hydroxyl, amino, $C_1$–$C_6$-alkylamino, di-$C_1$–$C_6$-alkylamino or tri-$C_1$–$C_6$-alkylamino, and R is a saturated or unsaturated $C_{12}$–$C_{24}$-alkyl radical.

Especially for topical administration, but also in compositions for other kinds of administration, it has proved to be especially favorable to use the compounds of the formula I or I' together with at least one alkylglycerol with 2 to 9 carbon atoms in the alkyl radical, which can be present in the form of an ether group attached to one of the primary or secondary OH groups of the glycerol. Such alkylglycerols increase or improve the action of the compounds of formula I or I' synergistically. Alkylglycerols with 3 to 9 C-atoms alone or in mixtures are preferred.

Therefore, a synergistically acting composition which exhibits especially favorable actions contains a) at least one compound of the formula $$R-Y-PO^{\ominus}{}_2-X-R_1 \quad (I)$$

or a physiologically acceptable salt thereof, wherein R is a saturated or unsaturated hydrocarbon radical of 12 to 24 C-atoms which may also be halogen-substituted, X is oxygen, —NH— or —NR$_2$—, and Y is oxygen or —NH—, R$_1$ is $C_1$–$C_8$-alkyl, $C_2$–$C_8$-alkyl which is unsaturated and/or substituted with halogen, amino, $C_1$–$C_6$-alkylamino, di-$C_1$–$C_6$-alkylamino, tri-$C_1$–$C_6$-alkylamino, hydroxyl, carboxyl, $C_3$–$C_8$-cycloalkyl or phenyl; 2-tert.butyloxycarbonylaminoethyl, 2-tert.butyloxycarbonylethyl, 2,3-isopropylidenedioxypropyl(1), 2,3-dibenzyloxypropyl-(1), 1,3-dibenzyloxypropyl-(2); N—$C_1$–$C_6$-alkylamino-$C_2$–$C_6$-alkyl if X is oxygen; 2,3-dihydroxypropyl-(1) if X is —NH—; and R$_2$— is 2,3-dihydroxypropyl(1) ; $C_1$–$C_8$-alkyl; or $C_2$–$C_8$-alkyl group which is unsaturated and/or substituted with halogen, amino, $C_1$–$C_6$-alkylamino, di-$C_1$–$C_6$-alkylamino, tri-$C_1$–$C_6$-alkylamino, hydroxyl, carboxyl, $C_3$–$C_8$-cycloalkyl or phenyl; and b) an alkylglycerol of the formula

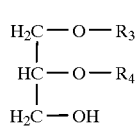

in which one of R$_3$ and R$_4$ is alkyl of 2 to 9 carbon atoms and the other is hydrogen, as well as optionally conventional inert pharmaceutical additives or diluents.

In the following, such a mixture is also called a cascade.

The content of a compound of the formula I or I' in mg/ml of cascade is indicated by a subscript For example, a cascade mixture which contains 5 mg/ml of a compound of the formula I or I' is designated as cascade$_5$, and a mixture of 200 mg of a compound of the formula I or I' per ml of cascade is designated as cascade$_{200}$.

The preparation of the alkylglycerols is known, for example, from German Offenlegungsschrift 33 43 530.

Alkylglycerol-water mixtures which contain, for example, nonylglycerol, octylglycerol, hexylglycerol, pentylglycerol, propylglycerol and ethylglycerol are preferred. Preferably, such aqueous mixtures contain 3 of the said glycerol ethers, namely, a lower (ethyl, propyl), a middle (pentyl, hexyl) and a higher (nonyl, octyl) alkyl glycerol, where the amount by weight of the lower ether is about as great as the sum of the amounts by weight of the two other glycerol ethers. The amount of water is about the same as the amount of lower glycerol ether and amounts, for example, to half of the total amount of the glycerol ethers present. Examples for such glycerol ether-water mixtures are set out in the following:

|  | water | glycerol propyl ether | glycerol hexyl ether | glycerol nonyl ether |
|---|---|---|---|---|
| parts by weight | 2 : | 2 : | 1 : | 1 |

|  | water | glycerol ethyl ether | glycerol pentyl ether | glycerol octyl ether |
|---|---|---|---|---|
| parts by weight | 2 : | 2 : | 1 : | 1 |

The therapeutic compositions of the present invention are especially suitable for topical administration. In order to treat skin tumors or skin metastases the composition is rubbed into the skin areas in question two to three times daily, for example with cascade$_5$ to cascade$_{200}$. Harmful side effects have until now not been observed, even in patients who have been treated daily over a period of 3 months. The remission of the skin metastases is accompanied by a normalization of the skin, which could be clearly demonstrated by tissue sections. Several patients with skin metastases were treated in this way and a complete disappearance of the mammary carcinoma skin metastases was observed.

The topical treatment with the preferred compositions of the present invention in the formulation $cascade_5$ to $cascade_{200}$ can also be used for the treatment of internal tumors or metastases by rubbing them into large surfaces of the skin. Therapeutically effective blood levels are thereby achieved by absorption through the skin. An advantage of this mode of administration lies in the fact that the compositions $cascade_5$ to $cascade_{200}$ are tolerated by the skin without problems.

This preferred type of composition of the medicament according to the invention in the form of $cascade_5$ to $cascade_{200}$ is also well suited for the preparation of suppositories for rectal insertion. Internal tumors and internal metastases can also be effectively treated therewith.

Another route of administration of the composition of this invention is instillation into pre-formed body cavities This type of administration is especially suitable for pleural carcinosesa malignant ascites, malignant pericardial discharges and bladder carcinomas In this case,, the anti-tumor compounds of the formula I are used either alone or in combination with conventional inert carriers or diluents, especially also with cascades.

For the systemic administration, oral or intravenous administration is effective.

For oral administration, the compounds of the formula I are advantageously used in the form of a potable solution. Suitable potable carriers for this purpose are milk, cocoa, fruit juice or drinking water. The preparation of such a potable solution can take place, for example, by diluting a concentrated alcoholic solution of a compound of the formula I or I' with water or with another one of the previously mentioned carriers. In the case of rats, daily doses of 20, 40 and 60 mg/kg body weight of oleyl-phosphocholine, lead to a complete remission of chemically-induced mammary carcinomas These compounds proved to be more effective and more compatible than 1-octadecyl-2-methyl-rac-glycero-3-phosphocholine. The tumor model used for these experiments was a so-called hard model. This means that the findings obtained with this model can also be applied to humans.

For intravenous administration via intravenous infusion therapy, the compounds of the formula I or I' are expediently used in physiological salt solution. Other infusion solutions may also be used. Dosage in humans for such solutions is, for example, 1–10 mg/kg body weight Finally, several types of administration of the compositions according to the invention can be used in combination, where the special topical compatibility has the result that rubbing into the skin is combined with another form of administration.

A further carrier mixture for the compounds of the formula I or I', which has proved to be especially useful, consists of a mixture of about 4 parts by weight of propylglycerol and 2 parts by weight of hexylglycerol and nonylglycerol each The topical use of the composition according to the invention in the especially preferred form of $cascade_5$ to $cascade_{200}$ over a period of time of several months showed that the local toxicity is limited to an increased desquamation of the skin, similar to the localized use of acetylsalicyclic acid.

Thus, the invention makes available novel therapeutic compositions for the treatment of tumors and provides not only a further anti-tumor agent but provides, for the first time, an agent which, as has been proven in clinical experiments, is also effective in the case of topical use. New possibilities are thereby opened up for the treatment of tumor patients.

For the preparation of therapeutic compositions, at least one compound of the formula I or I' is combined with conventional pharmaceutical carrier materials, diluents or other adjuvant materials to form pharmaceutical compositions in therapeutically usable form. For example, a compound of the formula I or I', or a physiologically acceptable salt thereof, is admixed or homogenized with conventional carriers, diluents or adjuvants at temperatures between 20 and 120° C., preferably between 30 and 100° C., the mixture obtained thereby is processed into dosage unit compositions containing 5 to 2000 mg, preferably 10 to 500 mg, especially 30 to 400 mg of the active ingredient of the formula I or I' per dose, and the composition is filled into hollow cells or capsules of appropriate size, or the composition if granulated and, after optionally adding further adjuvants, the granulate is compressed into tablets.

For example, a compound of the formula I or I' is admixed with starch, cellulose, lactose, formalin-casein, modified starch, magnesium stearate, calcium hydrogen phosphates, highly dispersed silicic acid, talcum, phenoxyethanol or mixtures of two or more of these inert carriers, the resulting mixture is granulated, optionally with an aqueous solution of gelatin, starch, polyvinylpyrrolidone, vinylpyrrolidone-vinyl acetate copolymer, polyoxyethylsorbitol monooleate or a mixture of these, the granulate is homogenized optionally with one or more of the above mentioned adjuvants, and the homogenized granulate is compressed into tablets or is filled into capsules, each containing a dosage unit of 5 to 2000 mg of active ingredient of the formula I or I'. Alternatively, a compound of the formula I or I' or a physiologically acceptable salt thereof is suspended or homogenized in molten hard fat after the addition of soybean lecithin as well as optionally 0.1 to 0.5 parts by weight of phenoxyethanol, based on 1 part by weight of compound I or I', at a temperature between 33 and 37° C., and the mixture is poured into hollow cells of suitable size to form dosage units containing 5 to 2000 mg of active ingredient as well as optionally 0.1 to 0.5 parts by weight of phenoxyethanol, based on 1 part by weight of compound I or I'. A compound of the formula I or I' or a physiologically acceptable salt thereof may also be homogenized at a temperature between 50 and 120° C., preferably between 50 and 100° C., optionally in the presence of one or more emulsifiers or 0.1 to 0.5 parts by weight of phenoxyethanol, based on 1 part by weight of compound I or I', with paraffin, vaseline, aliphatic alcohols of 12 to 25 carbon atoms, aliphatic monocarboxylic acids of 15 to 20 carbon atoms, sorbitol monopalmitate, polyoxyethylene-polyol fatty acid esters or a mixture of these, the mixture thus obtained is emulsified between 50 and 120° C. with water, optionally after the addition of a polyhydroxy lower aliphatic alcohol or phenoxyethanol. Finally, a compound of the formula I or I' or a physiologically acceptable salt thereof may be dissolved in water or vegetable oil, optionally in the presence of 0.1 to 0.5 parts by weight of phenoxyethanol, based on 1 part by weight of compound I or I', as well as optionally in the presence of an emulsifier, at a temperature between 30 and 100° C., and the solution thus obtained is diluted with an amount of water or vegetable oil so that the final solution contains 0.05 to 10% by weight, preferably 0.1 to 5% by weight of active ingredient of the formula I or I'.

Suitable emulsifiers are, for example, non-ionic emulsifiers as well as ionic emulsifiers. Examples of non-ionic emulsifiers are triglyceride mixtures of saturated vegetable fatty acids with 8, 10 and 12 carbon atoms, or emulsifiers based on polyaddition products of ethylene oxide, such as alkyl- and acyl-substituted polyaddition products of ethylene oxide, polyethylene glycol fatty acid esters, reaction products of ethylene oxide with castor oil or hydrogenated castor oil, ester of hydrogenated castor oil fatty acids with oxyethylated glycerol. The non-ionic emulsifiers may also be based on fatty acid amides or fatty acid condensation products with hydrophilic groups. Examples of ionic emulsifiers are emulsifiers based on fatty acid monoesters of glycerol or other polyhydroxy alcohols (lunacera alba).

If, in the preparation of the therapeutic compositions described above, the active ingredient of the formula I or I' is used together with a glycerol ether of the formula II or a mixture of such glycerol ethers, a synergistic enhancement of the anti-tumor action is observed.

For this purpose, the active ingredients of the formula I or I' are used with 1 to 30 parts by weight, preferably 2 to 20 parts by weight, based on 1 part by weight of compound I or I', of at least one glycerol ether of the formula II or a mixture of such glycerol ethers, as well as optionally 0.5 to 30 parts by weight, preferably 1 to 20 parts by weight of water, also based on 1 part by weight of compound I or I'. The glycerol ethers may be admixed with the compound of compounds of the formula I or I' at the beginning or also in a later stage of preparation of the therapeutic compositions according to the present invention.

The compounds of the formulas I and I' exhibit very effective anti-tumor action against 7,12-dimethylbenzanthracene-induced mammary cancer of the rat, as well as against methyl-nitrosourea-induced mammary carcinoma of the rat.

For example, a dose of 10 mg/kg body weight of rat achieves a growth cessation of the tumors, and higher doses also cause a complete disappearance of the growth.

The lowest already active dose is 5 mg/kg perorally and 5 mg/kg intravenously. The general effective dose range in the animal model described above is 5 to 50 mg/kg, especially 15 to 32 mg/kg both per orally and intravenously.

The direction of action of the compounds according to the invention is comparable with the action of the known medicament tamoxifen but, the action is stronger and of longer duration than that of tamoxifen.

Indications for the compounds according to the invention are mammary cancer and other human types of cancer.

The pharmaceutical compositions contain, in general, between 5–2000 mg, for example 10–400 mg of the compounds according to the invention.

The administration can take place, for example, in the form of tablets, capsules, pills, dragees, cones, salves, gels, creams, powders, dusting powders, aerosols or in liquid form. Examples of liquid forms of administration, are oily or alcoholic or aqueous solutions, as well as suspensions and emulsions Preferred forms of administration are tablets which contain between 40 and 400 mg or solutions which contain between 0.1 and 5% of active substance The individual dose of the active components according to the invention can be, for example a) in the case of oral medicinal forms between 5–100 mg/kg body weight, preferably 15–50 mg/kg body weight, b) in the case of parenteral medicinal forms (for example intravenous, intramuscular) between 5–100 mg/kg body weight, c) in the case of medicinal forms for local administration to the skin and mucous membranes (for example in the form of solutions, lotions, emulsions, ointments and so forth) between 50–2000 mg, preferably 80–1500 mg. (The doses are, in each case, referred to the free base).

For example, 1 tablet with a content of 40–400 mg of active substance can be administered 3 times daily or, for example, in the case of intravenous injection, 1–5 times daily one ampoule of 1–5 ml containing 50–250 mg of substances. In the case of oral administration, the minimum daily dose is, for example, 120 mg, the maximum daily dose in the case of oral administration should not be more than 100 mg/kg body weight.

The acute toxicity of the compounds according to the invention on the mouse (expressed by the LD 50 mg/kg; method according to Miller and Tainter; Proc. Soc. Exper. Biol. a. Med. 57 (1944) 261)) is for example, in the case of oral administration, between 200 and 450 mg/kg body weight.

The compositions can be used in human medicine, veterinary medicine, as well as in agriculture, alone or in admixture with other pharmacologically active materials.

The following examples illustrate the present invention and will enable others skilled in the art to understand it more completely. It should be understood, however, that the invention is not limited solely to the particular examples given below.

EXAMPLE 1

Hexadecylphosphoethanolamine
(phosphorylation, ring closure and ring opening)

Hexadecanol (1 mol, 243 g) and triethylamine (1.8 mol, 180 g) are dissolved in 1.5 liters of THF (tetrahydrofuran) and the solution is added dropwise to a vigorously stirred solution of phosphorus oxychloride (1.2 mol, 184 g) in 120 ml of THF in such a manner that the temperature in the reaction vessel (three-necked, 5 liters, with dropping funnel, thermometer and stirrer) does not exceed 10° C. For the acceleration of the procedure, the reaction vessel is cooled with an ice-salt mixture. Immediately after the dropwise addition, the reaction is concluded (detection via TLC in ether: Rf values of 0.8 for the starting product, of 0.0 for the reaction product after hydrolysis with water)

One removes the ice bath and drops into the reaction mixture, with vigorous stirring, a solution of ethanolamine (1.5 mols, 92 g) and triethylamine (1.8 mols, 180 g) in 1 liter of dioxane in such a manner that the temperature in the reaction vessel increases to 65 to 70° C. The ring formation is then concluded (detection by TLC in ether: Rf value of 0.2). One filters off from precipitated triethylamine hydrochloride while still warm and mixes the filtrate at 40 to 50° C. with 1.5 liters of 2N formic acid. After 15 minutes the ring opening is concluded (detection by TLC in ether: Rf value 0.0; TLC in chloroform/methanol/acetic acid/water 100:60:20:5 in vol.; Rf value 0.8). One cools to −20° C. and filters off the precipitate which consists substantially of pure hexadecylphosphoethanolamine. In the case of slight impurities, a chromatographic purification follows (see Example 2). Microanalysis (M.W. 365.50):

calc. (%): C 59.15 H 11.03 N 3.83 P 8.48 found (%): 59.01 10.95 3.79 8.31

EXAMPLE 2

2-Hexadecylphosphoethanolamine
(phosphorylation, ring closure, ring opening)

The reaction takes place as described in Example 1 but for 0.1 mol. In order to achieve good yields, the phosphorylation conditions must be somewhat modified, i.e., the temperature in the phosphorylation step is increased to 25° C. Otherwise one proceeds and works up as described.

Microanalysis (H.W. 365.50)

calc. (%) C 59.15 H 11.03 N 3.83 P 8.48 found (%) 58.96 10.91 3.69 8.39

EXAMPLE 3

Oleylphosphomethyl ester, sodium salt + 1 $H_2O$ (phosphorylation, methanolysis and LiBr cleavage)

The phosphorylation step takes place as in Example 1. For the methanolysis, the reaction mixture is mixed with methanol (10 moles 320 g) and triethanolamine (1.8 mols, 180 g) at 20° C. The methanolysis is concluded after 30 minutes. One mixes with 1.5 liters of hexane and 1.5 liters of water, shakes thoroughly and removes the solvent from the hexane phase. The oily residue is boiled under reflux with LiBr (2 mols, 174 g) in 1.5 liters of ethyl methyl ketone. After one hour, the reaction is complete. One removes the solvent, takes up in a mixture of 1 liter of methanol/water/chloroform, shakes thoroughly and isolates the lower chloroform phase which contains the product. For the conversion into the sodium salt, one treats the chloroform phase with 1 liter of saturated NaCl solutions. The chloroform phase is isolated and evaporated. One purifies the product by chromatography on silica gel.

Microanalysis (M.W. 402.50)

calc. (%): C 56.70 H 10.02 P 7.70 found (%): 56.65 9.98 7.45

The allyl ester was prepared correspondingly, as were the methyl- and allylphosphoric acid esters with tetradecanol, hexadecanol, octadecanol and eicosanol.

EXAMPLE 4

Hexadecylphosphohexyl ester, sodium salt + 1 $H_2O$ (phosphorylation with phosphorus oxychloride, phosphorylation with hexadecylphosphoric acid dichloride, methanolysis, cleavage with LiBr)

The phosphorylation of hexadecanol takes place as described in Example 1. The reaction mixture is further reacted directly with dropwise addition of hexanol (1.5 mols, 303 g) and triethanolamine (1.8 mols, 180 g) in 1.5 liters of THF. The temperature is now increased to 30° C. After two hours, the reaction has finished.

Methanolysis as well as the LiBr cleavage take place as described in Example 5.

Microanalysis (H.W. 446.59)

calc. (%): C 59.17 H 10.83 P 6.94 found (%): 59.08 10.74 6.71

The following alkyl esters were prepared analogously: hexadecylphosphobutyl, -octyl, -decyl and -dodecyl ester.

EXAMPLE 5

Hexadecylphosphoglycol ester, sodium salt + 1 $H_2O$ (phosphorylation, ring closure with glycol, ring opening)

The phosphorylation takes place as described in Example 1. The reaction mixture is further reacted directly with the dropwise addition of ethylene glycol (1.5 mols, 93 g) and triethanolamine (1.8 mols, 180 g) in 1.5 liters of THF. For the completion of the ring formation, the temperature is increased to 60° C. After 2 hours at this temperature, the reaction is concluded. One filters off the precipitated triethanolamine hydrochloride over a porcelain frit and mixes the filtrate, while vigorously stirring at 20° C., with 1.5 liters of water. After 2 hours, the hydrolysis has finished. One removes the solvent from the upper THF phase by evaporation in a vacuum The residue is mixed with a mixture of chloroform/methanol/half saturated NaCl solution, shaken, and phase separation is awaited. The lower chloroform phase contains the product. One removes the solvent and purifies the product by chromatography (Example 2).

Microanalysis (M.W. 406.48)

calc. (%): C 53.19 H 9.92 P 7.62 found (%): 53.07 9.73 7.53

The following glycol esters were prepared analogously: tetradecylphosphoglycol ester, octadecylphosphoglycol ester, oleylphosphoglycol ester.

EXAMPLE 6

Hexadecylphospho-hydroxyethylamide, sodium salt + 1 $H_2O$ (phosphorylation, ring closure with ethanolamine, opening with potassium carbonate in water)

The phosphorylation takes place as described in Example 1, as does the ring closure. After removal of the triethylamine hydrochloride, the filtrate is mixed, while vigorously stirring, with 1 liter 1M potassium carbonate solution in water. After 1 hour, the ring opening is finished. One removes the solvent in the upper THF phase, takes up in a mixture of 1 liter of chloroform/methanol/half saturated NaCl solution, shakes well and separates the chloroform phase. After removal of the solvent, the product is chromatographed and purified on silica gel.

Microanalysis (H.W. 405.50)

calc. (%): C 53.32 H 10.19 N 3.46 P 7.64 found (%): 53.26 10.07 3.21 7.59

The following compounds were prepared analogously tetradecyl, octadecyl-, oleylphospho-hydroxyethylamide.

EXAMPLE 7

Hexadecylphosphoglycerol, sodium salt + 1 $H_2O$ (phosphorylation with phosphorus oxychloride, phosphorylation with the phosphoric acid dichloride formed thereby, methanolysis, LiBr cleavage, hydrolysis in 70% acetic acid)

The phosphorylation corresponds to Example 1. The reaction mixture is further reacted directly with dropwise addition of 1,2-isopropylidene-glycerol (1.5 mols, 198 g) and triethylamine (1.8 mols, 180 g) in 15 liters of THF. After the dropwise addition, the temperature is increased to 30° C. The reaction is finished after two hours. Methanolysis takes place according to Example 5, as does the LiBr cleavage. The reaction product, sodium salt, is taken up in 2 liters of 70% acetic acid and heated to 60° C. The resultant acetone is removed in a slight vacuum (waterpump vacuum). The reaction is concluded after 2 hours, one mixes with 2 liters of water and extracts with 2 liters of chloroform. The chloroform phase is treated with 2 liters of 0.5 M sodium carbonate solution and, after phase separation, separated. One removes the solvent and chromatographs on silica gel.

Microanalysis (M.W. 436.51)

calc. (%): C 52.28 H 9.70 P 7.10 found (%): 52.13 9.59 6.91

The following glycerol esters were prepared analogously: tetradecyl-, octadecyl-, oleylphosphoglycerol.

EXAMPLE 8

Hexadecylphosphoric acid (N,N)-bis-(chloroethyl)-amine, Na salt + $H_2O$ (phosphorylation with phosphorus oxychloride, amide formation with bis-(chloroethyl)-amine, hydrolysis)

The phosphorylation step corresponds to Example 1. The reaction mixture is further reacted directly with the dropwise addition of bis-(chloroethyl)-amine in 1.0 liters of THF. Thereafter, triethylamine (0.4 mols, 40 g) in 0.5 liters of THF is added thereto. After 3 hours at 20° C., the reaction is finished. One separates the precipitated triethylamine hydrochloride over a porcelain frit and mixes the filtrate, while vigorously stirring, with 1 liter 1M acetic acid for hydrolysis. After 4 hours, the upper THF phase is separated, freed from solvent and taken up in 1 liter of chloroform/methanol/0.5 M sodium carbonate. The chloroform phase is removed, the solvent is removed therefrom, and the product is purified by chromatography on silica gel.

Microanalysis (M.W. 486.452)

calc. (%): C 49.38 H 8.91 Cl 14.58 N 2.88 P 6.37 found (%): 49.21 8.75 14.11 2.76 6.31

The following compounds were prepared analogously: tetradecyl-, octadecyl- oleylphosphoric acid- (N N) -bis-(chloroethyl)-amide.

Examples of pharmaceutical compositions

Example of a solution 25 g of 1-n-propyloxy-2,3-propanediol, 12.5 g of 1-n-hexyloxy-2,3-propanediol, 12.5 g of 1-n-nonyloxy-2,3-propanediol, 44 g of water and 1 g of phenoxyethanol are mixed and 5 g of hexadecylphosphoglycerol are dissolved in this mixture. The solution is freed from visible particles by filtration over suitable filters.

1 g of solution contains 50 mg of hexadecylphosphoglycerol.

Example of an ointment 5 g of hexadecylphosphoglycerol are suspended in 35 g of very viscous paraffin, 30 g of emulsifying cetylstearyl alcohol and 30 g of white vaseline are added thereto and melted. The melt is stirred until cool. A homogeneous active material distribution is achieved by working up of the cooled melt by means of a suitable homogenizing apparatus (for example a three-roll mill). 1 g of the hydrophilic salt contains 50 mg of hexadecylphosphoglycerol.

Example of an emulsion 1183 g of 1-n-propyloxy-2,3-propanediol, 5.91 g of 1-n-hexyloxy-2,3-propanediol, 5.91 g of 1-n-nonyloxy-2,3-propanediol, 20.35 g of water and 10 g of phenoxyethanol are mixed and 5 g of hexadecylphosphoglycerol dissolved in this mixture. 30 g of white vaseline, 15 g of cetyl alcohol and 5 g of sorbitol monopalmitate are melted on a waterbath, heated to 70° C. and the active material solution, also heated to 70° C. is emulsified in the fat phase with the aid of a high-speed dispersing apparatus Subsequently, the cream is cooled to 30° C., while stirring.

1 g of water-in-oil emulsion contains 50 mg of hexadecylphosphoglycerol.

Example of capsules 125 kg of hexadecylphosphoglycerol are dissolved in 5 kg of chloroform and 1.25 kg of Aerosil are suspended in this solution Subseguently, the solvent is removed in a vacuum. The dry mass is passed though a 1 mm sieve and once again dried in a vacuum at 30° C. in order to remove the last residues of solvent. The resulting granulate is filled in known manner with a suitable capsule machine into hard gelatin capsules, size 00, in an amount of 500 mg.

One capsule contains 250 mg of hexadecylphosphoglycerol.

Example of a lyophilizate 500 g of mannitol are dissolved in 3 liters of water for injection purposes in an atmosphere of nitrogen, 50 g of hexadecylphosphoglycerol are dispersed in the solution with the aid of a highspeed homogenization apparatus, and the dispersion is diluted to 4 liters with water for injection purposes. This milky dispersion is converted into a slightly opalescing colloid-disperse system by ultrasonic treatment or with the aid of a slot homogenizer.

Under aseptic conditions, the composition is now sterile filtered over a membrane filter of 0.22 µm pore width and filled in 40 ml amounts into 100 ml injection bottles in a nitrogen atmosphere One provides the bottles with freeze-drying stoppers and lyophilizes in a suitable plant. After drying, the lyophilizate is gassed with sterile, dry nitrogen, and the bottles closed in the plant. The stoppers are secured with a flanged cap.

For intravenous use, the lyophilizate is reconstituted in 100 ml of water for injection purposes. One bottle contains 500 mg of hexadecylphosphoglycerol.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A tumor inhibiting, therapeutic composition comprising:
   a. oleylphosphocholine or a physiologically acceptable salt thereof;
   b. an ethylglycerol ether or a propylglycerol ether,
   c. a pentylglycerol ether or a hexylglycerol ether, and
   d. an octylglycerol ether or a nonylglycerol ether, wherein "b" is present in an amount by weight which is about equal to the amount by weight of "c" and "d" combined.

2. The tumor inhibiting composition of claim 1, further comprising an amount of water equal in weight to about the amount of weight of "b".

3. The tumor inhibiting composition of claim 2, comprising, in parts by weight, two parts water, two parts propylglycerol ether, one part hexylglycerol ether, and one part nonylglycerol ether.

4. The tumor inhibiting composition of claim 2 comprising, in parts by weight, two parts water, two parts ethylglycerol ether, one part pentylglycerol ether, and one part octylglycerol ether.

* * * * *

UNITED STATES PATENT AND TRADEMARK OFFICE
CERTIFICATE OF CORRECTION

PATENT NO. : 5,916,884
DATED : June 29, 1999
INVENTOR(S) : Hansjörg Eibl

It is certified that error appears in the above-identified patent and that said Letters Patent is hereby corrected as shown below:

Title page, item [30], entitled Foreign Application Priority Data, change "Dec. 4, 1995 (DE) Germany 35 42 893" to - - Dec. 4, 1985 (DE) Germany 35 42 893.7 - -.

Signed and Sealed this

Twenty-seventh Day of June, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 5,916,884
DATED : Jun. 29, 1999
INVENTOR(S) : Hansjörg Eibl

Page 1 of 3

It is certified that error appears in the above-identified patent and that said Letters Patent is hereby corrected as shown below:

In column 17, line 38, change "1183" to -- 11.83 --.
In column 17, line 40, change "10 g" to --1.0 g --.
In column 2, line 49, change "9,1" to -- 9,10 --.

In column 1, line 55, change "modalities" to -- modalities. --.
In column 1, line 57, change "treatment" to -- treatment. --.
In column 2, line 9, the word "These" should be moved down one line to start a new paragraph.
In column 2, line 37, change "bromine" to -- bromine. --.
In column 2, line 43, change "molecules" to -- molecule. --.
In column 3, line 20, change "12" to -- 1,2 --.
In column 3, line 25, change "oleyl-phospho" to -- oleylphospho --.
In column 3, line 30, change "N.N,N" to --N,N,N --.

In column 3, line 37, change "groups" to --group,--.

In column 7, line 46, change "agents" to -- agent. --.
In column 8, line 34, change "agents" to -- agents. --.
In column 10, line 24, change "subscript" to -- subscript. --.
In column 11, line 19, change "cavities" to -- cavities. --.
In column 11, line 21, change "carcinosesa" to -- carcinoses, --.

UNITED STATES PATENT AND TRADEMARK OFFICE
CERTIFICATE OF CORRECTION

PATENT NO. : 5,916,884
DATED : Jun. 29, 1999
INVENTOR(S) : Hansjörg Eibl

It is certified that error appears in the above-identified patent and that said Letters Patent is hereby corrected as shown below:

In column 11, line 22, change "carcinomas" to -- carcinomas. --.
In column 11, line 22, change "In this case,," to -- In this case, --.

In column 11, line 36, change "oleyl-phosphocholine" to -- oleylphosphocholine --.

In column 11, line 38, change "cinomas" to -- cinomas. --.

In column 11, line 58, change "each" to -- each. --.

In column 13, line 55, change "emulsions" to -- emulsions. --.

In column 13, line 57, change "substance" to -- substance. --.

In column 14, line 42, insert a period at the end of the sentence, i.e. ... water)

In column 16, line 5, change "vacuum" to -- vacuum. --.

In column 16, line 50, change "2 hours, one" to -- 2 hours. One --.

In column 17, line 16, change "NN" to -- N.N --.

In column 17, line 46, change "apparatus" to -- apparatus. --.

In column 17, line 53, change "solution" to -- solution. --.

In column 17, line 53, change "subseguently" to -- subsequently --.

In column 17, line 51, change "125" to -- 1.25 --.

UNITED STATES PATENT AND TRADEMARK OFFICE
CERTIFICATE OF CORRECTION

PATENT NO. : 5,916,884
DATED : Jun. 29, 1999
INVENTOR(S) : Hansjörg Eibl

Page 3 of 3

It is certified that error appears in the above-identified patent and that said Letters Patent is hereby corrected as shown below:

In column 18, line 17, change "atmosphere" to -- atmosphere. --.

Signed and Sealed this

Twelfth Day of September, 2000

Attest:

Q. TODD DICKINSON

*Attesting Officer*   *Director of Patents and Trademarks*